United States Patent
Bell et al.

[11] Patent Number: 6,103,743
[45] Date of Patent: Aug. 15, 2000

[54] UNSATURATED AMINO ACID DERIVATIVES

[75] Inventors: Stanley Charles Bell, Narberth, Pa.; Kathleen Da Silva, Ontario, Canada; Allen Hopper, Somerset, N.J.; Methvin Isaac, Ontario, Canada; Eric A. Meade, Fanwood; Vassil Ilya Ognyanov, Princeton, both of N.J.; Abdelmalik Slassi, Ontario, Canada

[73] Assignee: Allelix Neuroscience, Inc., Salt Lake City, Utah

[21] Appl. No.: 09/369,686

[22] Filed: Aug. 6, 1999

[51] Int. Cl.$^7$ .................. A61K 31/44; A61K 31/195; A61K 31/24; A61K 31/21; A61K 31/38

[52] U.S. Cl. ................ 514/357; 514/567; 514/561; 514/539; 514/510; 514/357; 514/438; 560/36; 546/333; 549/77; 562/441

[58] Field of Search .................. 546/333; 549/77; 514/357, 438, 557, 513, 539, 567, 561, 510; 562/491, 441; 560/37, 36

[56] References Cited

PUBLICATIONS

Chemical Abstracts, citation 5199 g, vol. 64, Cyclization at carbon–carbon double bond. II. Synthesis of 4–substituted prolines by Pictet–Spengler reaction. p. 5199, 1966.

*Primary Examiner*—Zinna Northington Davis
*Assistant Examiner*—Binta Robinson Zi
*Attorney, Agent, or Firm*—Dechert Price & Rhoads

[57] ABSTRACT

Described herein are compounds having the general formula:

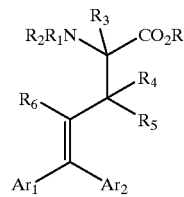

$Ar_1$ and $Ar_2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NRR'$, $NRR'$, $CO_2R$ (where R and R' are independently selected from the group consisting of H and alkyl) and a second aryl group, which may be substituted as above;

wherein any cycloalkyl or aryl substituent is linked to $Ar_1$ or $Ar_2$ by a bridging element which may be a single bond, a vinylene group, an ethynylene group, a Z group, a —Z—$(CH_2)_n$— group, a —$(CH_2)_n$—Z— group, or a —Z—$(CH_2)_n$—Z— group, where Z represents an O atom, a S atom, an NH group or an N-alkyl group, and n is an integer from 1 to 4;

wherein $Ar_1$ and $Ar_2$ may be attached to the central atom to which they are connected by a single bond, an alkylene, alkenylene or alkynylene group;

R is H, alkyl or the counter ion for a basic addition salt;

$R_1$ and $R_2$ are independently selected from the group consisting of H, alkyl and benzyl;
$R_3$, $R_4$, $R_5$ and $R_6$ are independently selected from the group consisting of H and alkyl;
and a stereoisomer, salt, solvate and hydrate thereof.

Also described is the use of these compounds as pharmaceuticals for the treatment of diseases in which inhibition of glycine transport via the GlyT-2 transporter is indicated.

20 Claims, No Drawings

UNSATURATED AMINO ACID DERIVATIVES

The present invention relates to a class of substituted amino acids, to pharmaceutical compositions containing them and to methods of treating neurological and neuropsychiatric disorders using such compounds.

Synaptic transmission is a complex form of intercellular communication that involves a considerable array of specialized structures in both the pre- and post-synaptic terminal and surrounding glial cells (Kanner and Schuldiner, *CRC Critical Reviews in Biochemistry*, 22, 1987:1032). Transporters sequester neurotransmitter from the synapse, thereby regulating the concentration of neurotransmitter in the synapse, as well as its duration therein, which together influence the magnitude of synaptic transmission. Further, by preventing the spread of transmitter to neighbouring synapses, transporters maintain the fidelity of synaptic transmission. Lastly, by sequestering released transmitter into the presynaptic terminal, transporters allow for transmitter reutilization.

Neurotransmitter transport is dependent upon extracellular sodium and the voltage difference across the membrane; under conditions of intense neuronal firing, as, for example, during a seizure, transporters can function in reverse, releasing neurotransmitter in a calcium-independent non-exocytotic manner (Attwell et al., *Neuron*, 11, 1993:401–407). Pharmacologic modulation of neurotransmitter transporters thus provides a means for modifying synaptic activity, which provides useful therapy for the treatment of neurological and psychiatric disturbances.

The amino acid glycine is a major neurotransmitter in the mammalian central nervous system, functioning at both inhibitory and excitatory synapses. By nervous system, both the central and peripheral portions of the nervous system are intended. These distinct functions of glycine are mediated by two different types of receptor, each of which is associated with a different class of glycine transporter. The inhibitory actions of glycine are mediated by glycine receptors that are sensitive to the convulsant alkaloid strychnine, and are thus referred to as "strychnine-sensitive". Such receptors contain an intrinsic chloride channel that is opened upon binding of glycine to the receptor; by increasing chloride conductance, the threshold for firing of an action potential is increased. Strychnine-sensitive glycine receptors are found predominantly in the spinal cord and brainstem, and pharmacological agents that enhance the activation of such receptors will thus increase inhibitory neurotransmission in these regions.

Glycine also functions in excitatory transmission by modulating the actions of glutamate, the major excitatory neurotransmitter in the central nervous system. See Johnson and Ascher, *Nature*, 325, 1987:529–531; Fletcher et al., *Glycine Transmission*, Otterson and Storm-Mathisen, eds., 1990:193–219. Specifically, glycine is an obligatory co-agonist at the class of glutamate receptor termed N-methyl-D-aspartate (NMDA) receptor. Activation of NMDA receptors increases sodium and calcium conductance, which depolarizes the neuron, thereby increasing the likelihood that it will fire an action potential. NMDA receptors are widely distributed throughout the brain, with a particularly high density in the cerebral cortex and hippocampal formation.

Molecular cloning has revealed the existence in mammalian brains two classes of glycine transporters, termed GlyT-1 and GlyT-2. GlyT-1 is found throughout the brain and spinal cord, and it has been suggested that its distribution corresponds to that of glutamatergic pathways and NMDA receptors (Smith, et al., *Neuron*, 8, 1992:927–935).

Molecular cloning has further revealed the existence of three variants of GlyT-1, termed GlyT-1a, GlyT-1b and GlyT-1c. Two of these variants (1a and 1b) are found in rodents, each of which displays a unique distribution in the brain and peripheral tissues (Borowsky et al., *Neuron*, 10, 1993:851–863; Adams et al., *J. Neuroscience*, 15, 1995:2524–2532). The third variant, 1c, has only been detected in human tissues (Kim, et al., *Molecular Pharmacology*, 45, 1994:608–617). These variants arise by differential splicing and exon usage, and differ in their N-terminal regions. GlyT-2, in contrast, is found predominantly in the brain stem and spinal cord, and its distribution corresponds closely to that of strychnine-sensitive glycine receptors (Liu et al., *J. Biological Chemistry*, 268, 1993:22802–22808; Jursky and Nelson, *J. Neurochemistry*, 64, 1995:1026–1033). Another distinguishing feature of glycine transport mediated by GlyT-2 is that it is not inhibited by sarcosine as is the case for glycine transport mediated by GlyT-1. These data are consistent with the view that, by regulating the synaptic levels of glycine, GlyT-1 and GlyT-2 selectively influence the activity of NMDA receptors and strychnine-sensitive glycine receptors, respectively.

Compounds which inhibit or activate glycine transporters would thus be expected to alter receptor function and, thus, provide therapeutic benefits in a variety of disease states. Inhibition of GlyT-2, for example, can be used to increase the activity of inhibitory neurons having strychnine-sensitive glycine receptors via increasing synaptic levels of glycine, thus diminishing the transmission of pain-related (i.e. nociceptive) information in the spinal cord, which has been shown to be mediated by these receptors (Yaksh, *Pain*, 37, 1989:111–123). Additionally, enhancing inhibitory glycinergic transmission through strychnine-sensitive glycine receptors in the spinal cord can be used to decrease muscle hyperactivity, which is useful in treating diseases or conditions associated with increased muscle contraction, such as spasticity (Truong et al., *Movement Disorders*, 3, 1988:77–89; Becker, *FASEB J*, 4, 1990:2767–2774). Spasticity associated with stroke, head trauma, multiple sclerosis, spinal cord injury, dystonia, and other conditions of illness and injury of the nervous system (such as epilepsy) can be treated via modulation of glycine transporters.

According to one aspect of the invention, there are provided compounds of Formula I:

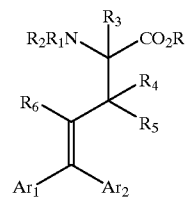

Formula I wherein:

$Ar_1$ and $Ar_2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NR'R''$, NR'R'', $CO_2R$ (where R' and R'' are independently selected from the group consisting of H and alkyl) and a second aryl group, which may be substituted as above;

wherein any cycloalkyl or aryl substituent is linked to $Ar_1$ or $Ar_2$ by a bridging element which may be a single bond, a vinylene group, an ethynylene group, a Z group, a —Z—$(CH_2)_n$— group, a —$(CH_2)_n$—Z— group, or a —Z—$(CH_2)_n$—Z— group, where Z represents an O atom, a S atom, an NH group or an N-alkyl group, and n is an integer from 1 to 4;

wherein $Ar_1$ and $Ar_2$ may be attached to the central atom to which they are connected by a single bond, an alkylene, alkenylene or alkynylene group;

R is H, alkyl or the counter ion for a basic addition salt;

$R_1$ and $R_2$ are independently selected from the group consisting of H, alkyl and benzyl;

$R_3$, $R_4$, $R_5$ and $R_6$ are independently selected from the group consisting of H and alkyl;

and a stereoisomer, salt, solvate and hydrate thereof.

Compounds of the invention inhibit glycine transport via the GlyT-2 transporter. By GlyT-2 we mean those glycine transporters found predominantly in the brain stem and spinal cord and the distribution of which corresponds closely to that of strychnine-sensitive glycine receptors (Liu et al. *J. Biological Chemistry*, 268, 1993:22802–22808; Jursky and Nelson, *J. Neurochemistry*, 64, 1995:1026–1033).

According to another aspect of the invention, there is provided a pharmaceutical composition comprising a compound of Formula I in an amount effective to inhibit glycine transport, and a pharmaceutically acceptable carrier.

In another aspect of the present invention there are provided compositions containing the present compounds in amounts for pharmaceutical use to treat medical conditions for which a glycine transport inhibitor is indicated, such as the treatment of pain, epilepsy or conditions associated with increased muscle contraction.

These and other aspects of the present invention are described in greater detail hereinbelow.

Definitions

The term aryl as used herein means a monocyclic aromatic group such as phenyl, pyridyl, furyl, thienyl and the like, or a bicyclic benzo-fused aromatic group such as naphthyl, indanyl, quinolinyl and the like.

The term alkyl as used herein means straight- and branched-chain alkyl radicals containing from one to six carbon atoms and includes methyl, ethyl, isopropyl and the like.

The term cycolalkyl as used herein means a carbocyclic ring containing from three to eight carbon atoms and includes cyclopropyl, cyclohexyl and the like.

The terms aralkyl and aralkyloxy as used herein means an alkyl radical substituted with an aryl or aryloxy group and includes benzyl, phenethyl, benzyloxy and the like.

The terms alkylene, alkenylene and alkynylene as used herein means straight- and branched-chain bivalent radicals containing from one to six carbon atoms, such as methylene, ethylene, vinylene, propenylene and ethynylene.

The term alkoxy as used herein means straight- and branched-chain alkoxy radicals containing from one to six carbon atoms and includes methoxy, ethoxy and the like.

The term alkanoyl as used herein means straight- and branched-chain radicals containing from one to six carbon atoms and includes acetyl, propionyl and the like.

The term halo as used herein means halogen and includes fluoro, chloro, bromo and the like.

DETAILED DESCRIPTION AND PREFERRED EMBODIMENTS

Compounds of Formula I include those in which $Ar_1$ and $Ar_2$ are, independently, optionally-substituted aryl groups. Preferably, $Ar_1$ is optionally-substituted phenyl, more preferably halo-substituted phenyl and, even more preferably, $Ar_1$ is a 2,4-difluorophenyl group.

Further, the aryl group which is in a cis conformation with respect to the glycine moiety (that is, group $Ar_2$) is preferably unsubstituted, or is substituted with a small group such as an alkyl or alkoxy group having up to 4 carbon atoms, or a halo group. More preferably, $Ar_2$ is alkyl-substituted phenyl, and, even more preferably, a 4-alkyl-substituted phenyl. Most preferably, $Ar_2$ is a 4-isopropylphenyl group.

Compounds of Formula I include those in which R is selected from the group consisting of H, alkyl and the counter-ion of a basic addition salt (such as $Na^+$). Preferably, R is selected from the group consisting of H and alkyl and, more preferably, R is H.

Compounds of Formula I include those in which $R_1$ and $R_2$ are selected from the group consisting H, alkyl and benzyl. Preferably, $R_1$ and $R_2$ are selected from the group consisting of H and alkyl and, more preferably, $R_1$ and $R_2$ are both H.

Compounds of Formula I include those in which $R_3$, $R_4$, $R_5$ and $R_6$ are selected from the group consisting H and alkyl. Preferably, $R_3$, $R_4$, $R_5$ and $R_6$ are selected from the group consisting of H and methyl and, more preferably, $R_3$, $R_4$, $R_5$ and $R_6$ are all H.

In specific embodiments of the invention, the compounds of Formula I include:

2-Amino-5,5-bis-[2,4-difluorophenyl]-4-pentenoic acid;
2-Amino-5,5-bis-[4-isopropylphenyl]-4-pentenoic acid;
E-2-Amino-5-[2-(3,5-difluorobenzyloxy)phenyl]-5-[4-isopropylphenyl]-4-pentenoic acid;
E-2-Amino-5-[2-(3,5-difluorobenzyloxy)phenyl]-5-phenyl-4-pentenoic acid;
E-2-Amino-5-[2,4-difluorophenyl]-5-[2-naphthyl]-4-pentenoic acid;
E-2-Amino-5-[2,4-difluorophenyl]-5-[3,4-dimethoxyphenyl]-4-pentenoic acid;
E-2-Amino-5-[2,4-difluorophenyl]-5-[3-isopropylphenyl]-4-pentenoic acid;
E-2-Amino-5-[2,4-difluorophenyl]-5-[3-nitrophenyl]-4-pentenoic acid;
E-2-Amino-5-[2,4-difluorophenyl]-5-[3-pyridyl]-4-pentenoic acid;
E-2-Amino-5-[2,4-difluorophenyl]-5-[3-thienyl]-4-pentenoic acid;
E-2-Amino-5-[2,4-difluorophenyl]-5-[4-cyanophenyl]-4-pentenoic acid;
E-2-Amino-5-[2,4-difluorophenyl]-5-[4-ethylphenyl]-4-pentenoic acid;
E-2-Amino-5-[2,4-difluorophenyl]-5-[4-isopropylphenyl]-2-methyl-4-pentenoic acid;
E-2-Amino-5-[2,4-difluorophenyl]-5-[4-isopropylphenyl]-4-pentenoic acid;

E-2-Amino-5-[2,4-difluorophenyl]-5-[4-methoxyphenyl]-4-pentenoic acid;
E-2-Amino-5-[2,4-difluorophenyl]-5-[4-methylphenyl]-4-pentenoic acid;
E-2-Amino-5-[2,4-difluorophenyl]-5-[4-<sup>n</sup>butylphenyl]-4-pentenoic acid;
E-2-Amino-5-[2,4-difluorophenyl]-5-[4-<sup>t</sup>Butylphenyl]-4-pentenoic acid;
E-2-Amino-5-[2,4-difluorophenyl]-5-[4-trifluoromethylphenyl]-4-pentenoic acid;
E-2-Amino-5-[2,4-difluorophenyl]-5-phenyl-4-pentenoic acid;
E-2-Amino-5-[2-biphenyl]-5-[2,4-difluorophenyl]-4-pentenoic acid;
E-2-Amino-5-[2-fluorophenyl]-5-[4-isopropylphenyl]-4-pentenoic acid;
E-2-Amino-5-[3,4-diethylphenyl]-5-[2,4-difluorophenyl]-4-pentenoic acid;
E-2-Amino-5-[3-biphenyl]-5-[2,4-difluorophenyl]-4-pentenoic acid;
E-2-Amino-5-[4-biphenyl]-5-[2,4-difluorophenyl]-4-pentenoic acid;
E-2-Amino-5-[4-biphenyl]-5-[4-isopropylphenyl]-4-pentenoic acid;
E-2-Amino-5-[4-ethylphenyl]-5-[4-fluorophenyl]-4-pentenoic acid;
E-2-Amino-5-[4-fluorophenyl]-5-[4-isopropylphenyl]-4-pentenoic acid;
E-2-Amino-5-[4-isopropylphenyl]-5-[4-methylphenyl]-4-pentenoic acid;
E-2-Amino-5-[4-isopropylphenyl]-5-[4-<sup>t</sup>butylphenyl]-4-pentenoic acid;
E-2-Amino-5-phenyl-5-[4-<sup>t</sup>butylphenyl]-4-pentenoic acid;
Z-2-Amino-5-[2,4-difluorophenyl]-5-[4-isopropylphenyl]-4-pentenoic acid;
Z-2-Amino-5-[2,4-difluorophenyl]-5-[4-<sup>t</sup>Butylphenyl]-4-pentenoic acid;
Z-2-Amino-5-[4-biphenyl]-5-[2,4-difluorophenyl]-4-pentenoic acid; and
Z-2-Amino-5-[4-isopropylphenyl]-5-phenyl-4-pentenoic acid.

In preferred embodiments of the invention, the compounds of Formula I include:
E-2-Amino-5-[2,4-difluorophenyl]-5-[4-methoxyphenyl]-4-pentenoic acid;
E-2-Amino-5-[4-biphenyl]-5-[4-isopropylphenyl]-4-pentenoic acid;
E-2-Amino-5-[3-biphenyl]-5-[3,4-diethylphenyl]-4-pentenoic acid;
2-Amino-5,5-bis-[4-isopropylphenyl]-4-pentenoic acid;
Z-2-Amino-5-[4-biphenyl]-5-[2,4-difluorophenyl]-4-pentenoic acid;
E-2-Amino-5-[4-biphenyl]-5-[2,4-difluorophenyl]-4-pentenoic acid;
E-2-Amino-5-[2-biphenyl]-5-[2,4-difluorophenyl]-4-pentenoic acid;
E-2-Amino-5-[4-isopropylphenyl]-5-[4-methylphenyl]-4-pentenoic acid; and
E-2-Amino-5-[2,4-difluorophenyl]-5-phenyl-4-pentenoic acid.

In more preferred embodiments of the invention, the compounds of Formula I include:
E-2-Amino-5-[2-(3,5-difluorobenzyloxy)phenyl]-5-phenyl-4-pentenoic acid;
E-2-Amino-5-[3-biphenyl]-5-[2,4-difluorophenyl]-4-pentenoic acid;
E-2-Amino-5-[2,4-difluorophenyl]-5-[3-isopropylphenyl]-4-pentenoic acid;
E-2-Amino-5-[3,4-diethylphenyl]-5-[4-fluorophenyl]-4-pentenoic acid;
E-2-Amino-5-[2,4-difluorophenyl]-5-[4-<sup>t</sup>Butylphenyl]-4-pentenoic acid;
E-2-Amino-5-[4-fluorophenyl]-5-[4-isopropylphenyl]-4-pentenoic acid; and
E-2-Amino-5-[2,4-difluorophenyl]-5-[4-trifluoromethylphenyl]-4-pentenoic acid.

In the most preferred embodiments of the invention, the compounds of Formula I include:
Z-2-Amino-5-[4-isopropylphenyl]-5-phenyl-4-pentenoic acid;
E-2-Amino-5-[4-ethylphenyl]-5-[4-fluorophenyl]-4-pentenoic acid;
E-2-Amino-5-[2-fluorophenyl]-5-[4-isopropylphenyl]-4-pentenoic acid;
E-2-Amino-5-[2,4-difluorophenyl]-5-[4-isopropylphenyl]-4-pentenoic acid;
E-2-Amino-5-[2,4-difluorophenyl]-5-[4-isopropylphenyl]-2-methyl-4-pentenoic acid;
E-2-Amino-5-[2-(3,5-difluorobenzyloxy)phenyl]-5-[4-isopropylphenyl]-4-pentenoic acid;
E-2-Amino-5-[3,4-diethylphenyl]-5-[2,4-difluorophenyl]-4-pentenoic acid;
E-2-Amino-5-[2,4-difluorophenyl]-5-[4-ethylphenyl]-4-pentenoic acid; and
E-2-Amino-5-[2,4-difluorophenyl]-5-[4-methylphenyl]-4-pentenoic acid.

Compounds of Formula I can be considered to be amino acids or derivatives thereof. Compounds which contain, instead of a carboxylate group, a "carboxylate equivalent" group, such as hydroxamic acids, phosphonic acids, phosphinic acids, sulfonic acids, sulfinic acids, amides or tetrazoles (or derivatives thereof) are also considered embodiments of the present invention.

In another embodiment of the invention the compound of Formula I is provided in labeled form, such as radiolabeled form, e.g. labeled by incorporation within its structure $^3$H or $^{14}$C or by conjugation to $^{125}$I. Such labeled compounds can be used to identify GlyT-2 transporter ligands by techniques common in the art. This can be achieved by incubating the transporter or tissue in the presence of a ligand candidate and then incubating the resulting preparation with an equimolar amount of radiolabeled compound of the invention. GlyT-2 transporter ligands are thus revealed as those that are not significantly displaced by the radiolabeled compound of the present invention. Alternatively, GlyT-2 transporter ligand candidates may be identified by first incubating a radiolabeled form of a compound of the invention then incubating the resulting preparation in the presence of the candidate ligand. A more potent GlyT-2 transporter ligand will, at equimolar concentration, displace the radiolabeled compound of the invention.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention.

The conversion of a given compound salt to a desired compound salt is achieved by applying standard techniques, well known to those skilled in the art.

The compounds of the present invention have at least one chiral centre. The invention extends to cover all structural and optical isomers of these compounds, as well as to racemic mixtures thereof.

Compounds of Formula I can be prepared using methods analogous to those known in the art. For example, as illustrated in Scheme 1, below, compounds of Formula I in which $R_6$ is H can be prepared from protected amino acids such as benzophenone imine derivative 5 which, upon treatment with propenyl bromide 4, gave intermediate iodoalkene 6 (note that the benzophenone imine is not the only protecting group which can be utilised in this scheme, any amine-protecting group which is stable under the reaction conditions described herein, and which may be readily removed without compromising the integrity of product 9, may be employed). Suzuki coupling of this iodide with diaryl boronic acid $(Ar_2)_2B(OH)_2$ gave diaryl alkene 7 which, after deprotection and hydrolysis, gave product 9.

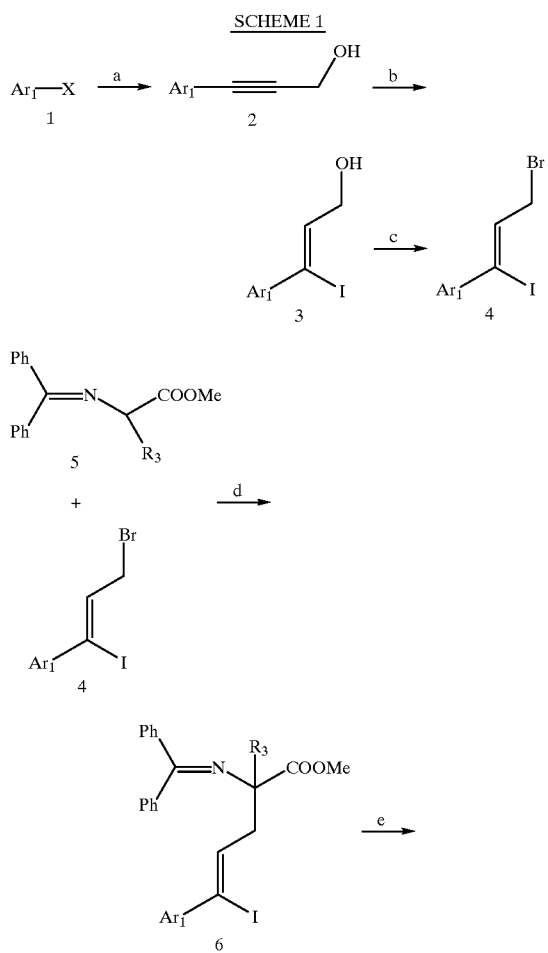

SCHEME 1

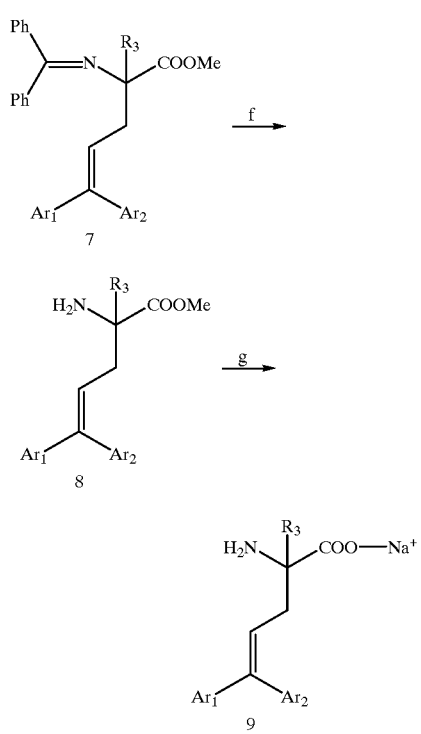

a) Pd(PPh$_3$)$_4$, CuI, propargyl alcohol, Et$_3$N;
b) Red-Al, I$_2$, ether;
c) PBr$_3$, CH$_2$Cl$_2$, 0°C.;
d) LDA, THF, HMPA, -78°C.;
e) (Ar$_2$)B(OH)$_2$, Pd(PPh$_3$)$_4$, DME/Na$_2$CO$_3$, 110°C.;
f) TFA, H$_2$O, CH$_2$Cl$_2$, rt;
g) ˉN NaOH, MeOH Alternatively, such compounds can be made according to the route shown in Scheme 2, below. In this approach, protected amino acid 5 was converted to the alkynyl intermediate 11 by treatment with acetylenic bromide 10. Iodide 13 (obtained via stannylated intermediate 12) was converted to diaryl alkene 7 using standard Suzuki coupling chemistry. Deprotection and hydrolysis of this intermediate gave the desired product, compound 9.

SCHEME 2

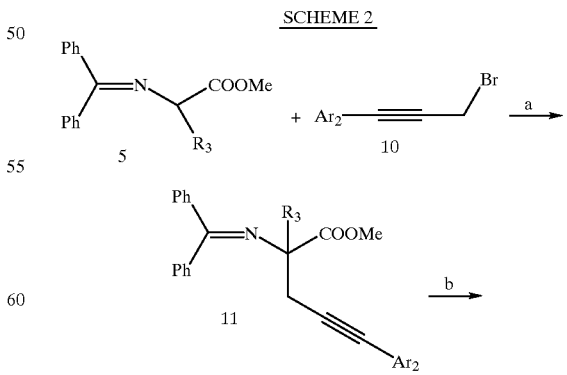

9
-continued

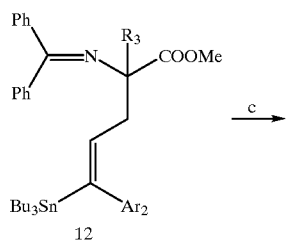
12

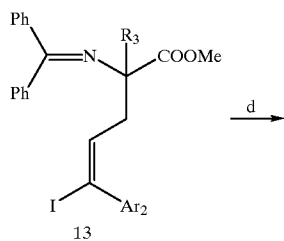
13

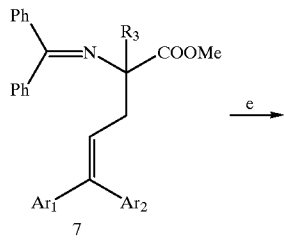
7

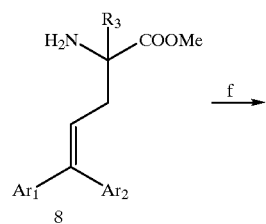
8

10
-continued

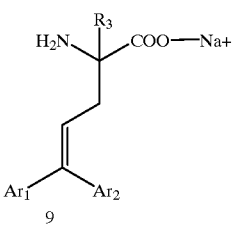
9 a) LDA, THF/HMPA;
b) Bu₃SnH, Pd(PPh₃)₂Cl₂, THF;
c) I₂, CH₂Cl₂;
d) Ar₁—B(OH)₂, Pd(PPh₃)₄,
e) DME/Na₂CO₃, 110°C.;
f) (I)TFA, H₂O, CH₂Cl₂, rt; (ii) 1N NaOH, MeOH

Schemes 1 and 2, above, are complementary approaches to the synthesis of compounds of the invention, in that the order in which the aryl groups Ar₁ and Ar₂ are introduced is complementary. This allows control of the geometry of the aryl groups about the double bond, as well as greater flexibility in the choice of synthetic routes for the preparation of compounds of the invention, which may be affected by factors such as the availability, or otherwise, of a particular starting material.

Scheme 2 also had the advantage that it allows preparation of compounds which could not be made using the route shown in Scheme 1. For example, some substituents (such as acetyl) are incompatible with the Red-Al reduction step b of Scheme 1, but such compounds can be made using Scheme 2.

Compounds of Formula I in which R₃ is other than H can be prepared according to Scheme 3, below. Alkylation of the dihydroimidazole glycine derivative 14 (prepared according to the method of Seebach et al., Eur. J. Org. Chem, 1337–1351, 1998) afforded compound 15. Treatment of this compound with 4 gave intermediate 16, which was converted to diaryl alkene 17 by Suzuki coupling with the appropriate arylboronic acid, as previously described. Deprotection and hydrolysis of intermediate 17, again as previously described, gave product 9.

SCHEME 3

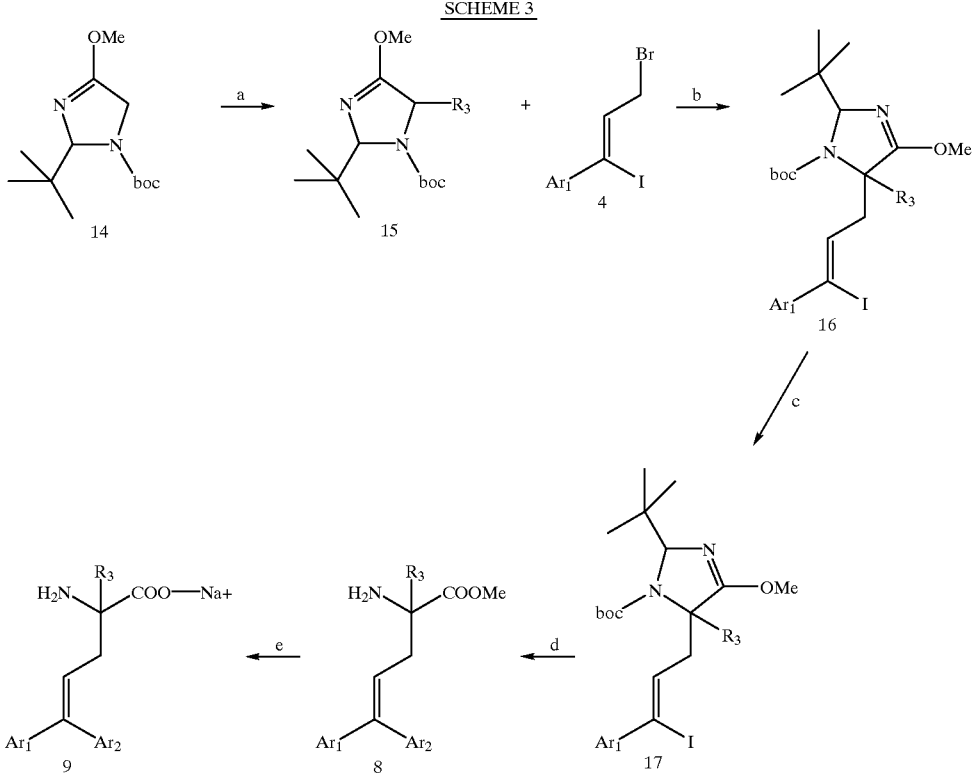

a) R₃X, LDA, THF;
b) LDA, THF;
c) Ar₂B(OH)₂, Pd(PPh₃)₄, DME, Na₂CO₃, 110°C.;
d) (i) 1N TFA, CH₂Cl₂, (ii) 2N TFA, CH₂Cl₂;
e) 1N NaOH, MeOH

Compounds of Formula I in which $R_6$ is other than H were prepared according to Scheme 4, below. Treatment of diaryl ketone 18 with (19) in the presence of base gave ester 20, which was reduced to alcohol 21 with Dibal. Treatment of this alcohol with phosphorous tribromide gave intermediate 22, which was treated with the protected amino acid 23 to give compound 24 which, in turn, after deprotection and hydrolysis in the usual way, gave product 25.

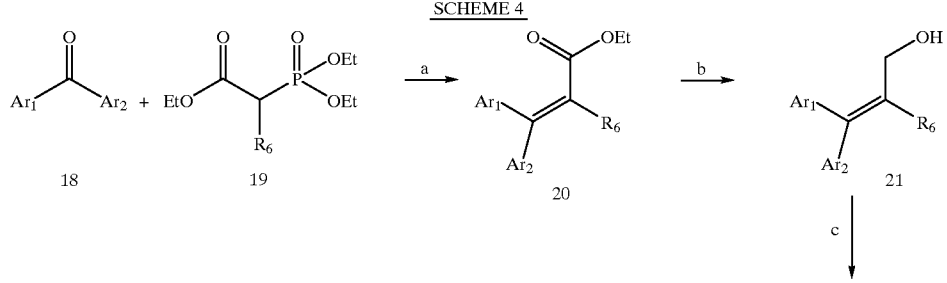

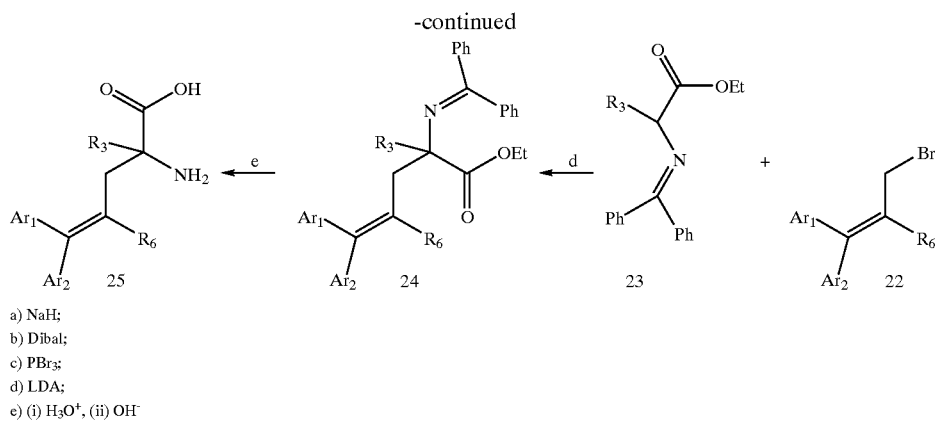

a) NaH;
b) Dibal;
c) PBr₃;
d) LDA;
e) (i) $H_3O^+$, (ii) $OH^-$

Compounds of Formula I in which groups $R_4$ and $R_5$ are other than H can be prepared using the chelate enolate Claisen Rearrangement chemistry of Kazmaier (U. Kazmaier et al., J. Org. Chem., 64, p4574–4575, 1999; and Synthesis, 1998, p1314–1320 and p1321–1326), as shown in Scheme 5, below. Treatment of diaryl ketone 18 with alkenyl lithium 26 gives allylic alcohol 27 which, upon treatment with acyl fluoride 29 (prepared by treatment of protected amino-acid 28 with cyanuric fluoride) gives ester 30. Claisen rearrangement of this ester gives product 31, having the geometry and stereochemistry shown. Finally, deprotection of the amino functionality with formic acid yields product 32.

acids can be prepared from the corresponding carboxylic acids by conversion to an N-hydroxysuccinimide ester followed by treatment with hydroxylamine. Amides are accessible by treatment of a methyl ester with ammonia in methanol. Tetrazoles can be prepared by reacting α-cyanohydroxyimines with sodium azide, followed by hydrogenation (see Lunn et al., J. Med. Chem., 35, 4608 (1992)).

Dialkyl-(1-aminoalkyl)-phosphonates 35 are available using the chemistry of Genet (J. P. Genet et al., Synthesis, 1990, p41–43), as shown in Scheme 6, below. Alkylation of protected aminophosphonate 33 with an alkyl halide in the presence of base gave intermediate 34 which, upon depro-

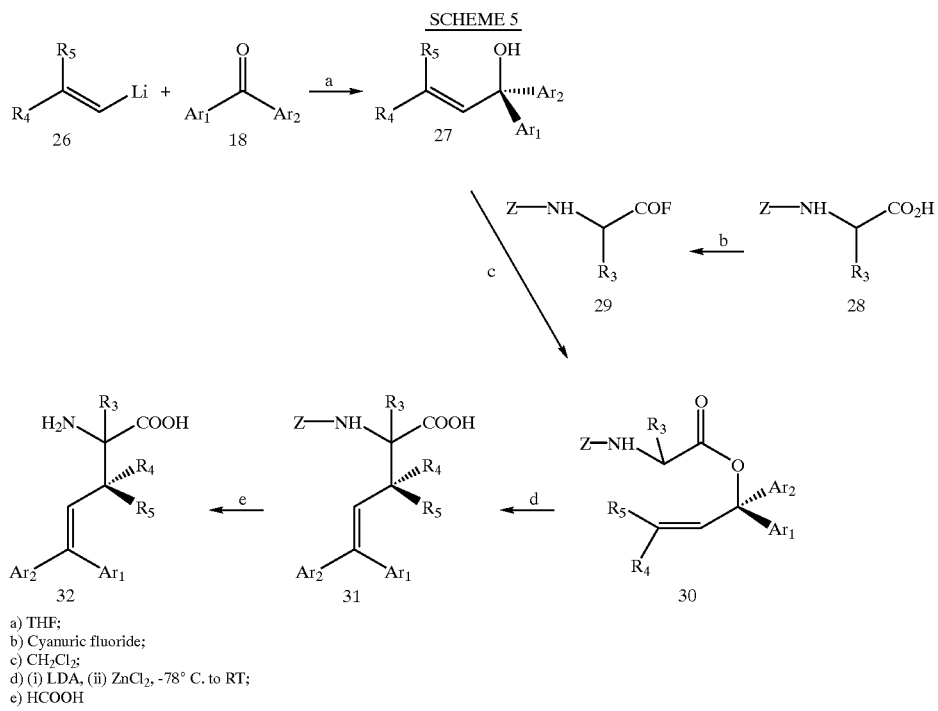

SCHEME 5 a) THF;
b) Cyanuric fluoride;
c) $CH_2Cl_2$;
d) (i) LDA, (ii) $ZnCl_2$, -78° C. to RT;
e) HCOOH Compounds of the invention which contain so-called "carboxylate equivalents" (as previously defined) can be prepared in a variety of ways. For example, hydroxamic tection gave phosphonate 35. Such phosphonates can be used in place of the protected amino acids in Schemes 1 and 2, above, to generate compounds of the invention.

15

SCHEME 6

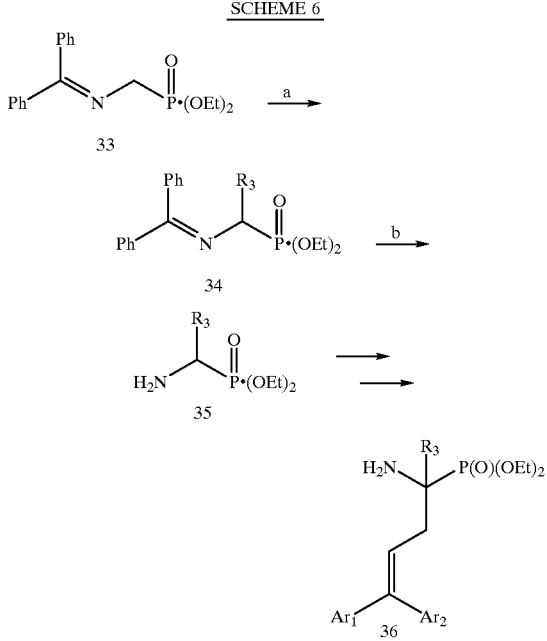

a) R$_3$X, KOH, Phase-transfer catalyst;
b) (i) 10% HCl, (ii) K$_2$CO$_3$

α-Aminophosphonic acids are also accessible utilising Genet chemistry (Genet et al., Tet. Left., 33, p77–80, 1992). In a similar fashion these, too, can be utilised to prepare phosphinic acid equivalents of compounds of Formula I.

Note that, in some cases, the chemistries outlined above may have to be modified, for instance by use of protecting groups, to prevent side reactions due to reactive groups, such as reactive groups attached as substituents. Such modifications will be obvious to one skilled in the art of synthetic organic chemistry.

It should also be noted that the compounds described in the above reaction schemes may be further functionalised to provide other compounds of the invention. For example, compounds wherein R$_1$ and R$_2$ are H can be alkylated using standard techniques well known in the art.

Compounds of the invention are useful as pharmaceuticals for the treatment of medical conditions for which GlyT-2-mediated inhibition of glycine transport is needed, such as the treatment of pain or the treatment of diseases or conditions associated with increased muscle contraction, for example spasticity and myoclonus. Spasticity that can be treated via modulation of glycine transporters is that associated with epilepsy, stroke, head trauma, multiple sclerosis, spinal cord injury, dystonia, and other conditions of illness and injury of the nervous system. By GlyT-2 we mean those glycine transporters found predominantly in the brain stem and spinal cord and the distribution of which corresponds closely to that of strychnine-sensitive glycine receptors (Liu et al. *J. Biological Chemistry*, 268, 1993:22802–22808; Jursky and Nelson, J. Neurochemistry, 64, 1995:1026–1033).

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 1 to 25 mg) of a compound of Formula I or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous or intramuscular dose of between 0.1 mg and 100 mg, preferably between 0.1 mg and 50 mg, e.g., between 1 mg and 25 mg, of a compound of Formula I or a pharmaceutically acceptable salt, solvate or hydrate thereof calculated as the free base, the compound being administered 1 to 4 times per day. Suitably, the compounds will be administered for a period of continuous therapy, for example for a week or more.

EXPERIMENTAL EXAMPLES

Example 1

Benzophenone-imine Glycine methyl ester (5)

To a flame dried 250 ml round bottom flask, flushed with Argon, was added glycine methyl ester hydrochloride (10.0 g, 79.64 mmol), benzophenone-imine (13.36 ml, 79.64 mmol) and $CH_2Cl_2$ (100 ml). The mixture was stirred at room temperature for 18 hrs, filtered and evaporated to dryness in vacuo. The concentrated yellow oil so obtained was then recrystallized, giving 19.96 g (98.94% yield) of the title product as a white solid.

Example 2

General Procedure for the synthesis of 3-Aryl-2-propyn-1-ols (2)

To a mixture of the Aryl iodide, 1 (1 eqv), $Pd(PPh_3)_4$ (0.1 eqv), and CuI (0.3 eqv) at room temperature was added $Et_3N$. The reaction mixture was cooled to 0° C. and propargyl alcohol (1.5 eqv) added. The mixture was then allowed to stir at room temperature for an additional 30 minutes, before filtration through a short pad of silica gel. The residue was washed with $CH_2Cl_2$ and the filtrate concentrated in vacuo. The crude product was then purified by flash chromatography.

The following compounds were prepared using the above protocol:

a) 3-[2,4-Difluorophenyl]-2-propyn-1-ol (3.5 g, quantitative yield) from 2,4-Difluoro-1-iodobenzene (5.0 g, 20.0 mmol);

b) 3-[4-lsopropylphenyl]-2-propyn-1-ol (3.5 g, 98% yield) from 4-Isopropyliodo-benzene (2.0 g, 8.1 mmol);

c) 3-[4-t-Butylphenyl]-2-propyn-1-ol (3.5 g, 98% yield) from 4-t-Butyliodobenzene (4.3 g, 20.2 mmol);

d) 3-[4,4'-Biphenyl]-2-propyn-1-ol (3.5 g, 98% yield) from 4-phenyl-4-iodobenzene (4.3 g, 20.2 mmol);

e) 3-[3,4-Diethylphenyl]-2-propyn-1-ol (2.2 g, 90% yield) from 1,2-Diethyl-4-iodo-benzene (3.4 g, 13.0 mmol);

f) 3-[2-(3,5-difluorobenzyloxy)phenyl]-2-propyn-1-ol;

g) 3-[2-fluorophenyl]-2-propyn-1-ol;

h) 3-[4-fluorophenyl]-2-propyn-1-ol;

i) 3-phenyl-2-propyn-1-ol.

Example 3

General Procedure for the synthesis of Z-3-Aryl-3-iodo-2-propen-1-ols (3)

To a solution of Red-Al (2 eqv) in ether at 0° C. was added alcohol 2. The mixture was allowed to stir at room temperature for 1 hr, re-cooled to 0° C., and quenched by the addition of ethyl acetate (1.2 eqv). The mixture was then further cooled to −78° C. and $I_2$ (1.6 eqv) added in one portion. The mixture was allowed to warm to room temperature and stirred for 2 hrs, after which it was quenched by the addition of saturated $Na_2S_2O_3$. The reaction mixture was then extracted with ethyl acetate, washed with brine and dried over $Na_2SO_4$ (anhydrous). The organic layer was concentrated in vacuo and purified by flash column chromatography.

The following compounds were prepared using the above protocol:

a) Z-3-[2,4-Difluorophenyl]-3-iodo-2-propen-1-ol (5.3 g, 80% yield) from 2a (3.7 g, 22.2 mmol);

b) Z-3-[4-Isopropylphenyl]-3-iodo-2-propen-1-ol (1.8 g, 76% yield) from 2b (1.4 g, 8.0 mmol);

c) Z-3-[4-t-Butylphenyl]-3-iodo-2-propen-1-ol (1.3 g, 64% yield) from 2c (1.2 g, 6.4 mmol);

d) Z-3-[4,4'-Biphenyl]-3-iodo-2-propen-1-ol (2.1 g, 87% yield) from 2d (1.5 g, 7.3 mmol);

e) Z-3-[2-(3,5-difluorobenzyloxy)phenyl]-3-iodo-2-propen-1-ol from 2f;

f) Z-3-[2-fluorophenyl]-3-iodo-2-propen-1-ol from 2g;

g) Z-3-[4-fluorophenyl]-3-iodo-2-propen-1-ol from 2h;

h) Z-3-phenyl-3-iodo-2-propen-1-ol from 2i.

Example 4

General Procedure for the synthesis of Z-3-Aryl-3-iodo-2-propenyl bromides (4)

To a solution of iodo-alcohol 3 (1.0 eqv) at 0° C. in $CH_2CO_2$ was added slowly $PBr_3$ (0.33 eqv). The reaction mixture was stirred at this temperature for 2 hrs, until judged complete by TLC. The mixture was poured into saturated $NaHCO_3$ and extracted with hexane or $CH_2Cl_2$. The organic extract was then washed with brine and dried over anhydrous $Na_2SO_4$. The organic solvent was removed in vacuo and the crude product was used directly in the next step without further purification.

The following compounds were prepared using the above protocol:

a) Z-3-[2,4-Difluorophenyl]-3-iodo-2-propenyl bromide (4.0 g, 63% yield) from 3a (5.3 g, 17.8 mmol);

b) Z-3-[4-lsopropylphenyl]-3-iodo-2-propenyl bromide (2.0 g, 91% yield) from 3b (1.8 g, 6.1 mmol);

c) Z-3-[4-t-butylphenyl]-3-iodo-2-propenyl bromide (1.4 g, 94% yield) from 3c (1.2 g, 4.0 mmol);

d) Z-3-[4,4'-Biphenyl]-3-iodo-2-propenyl bromide (0.6 g, 82% yield) from 3e (0.6 g, 1.8 mmol);

e) Z-3-[2-(3,5-difluorobenzyloxy)phenyl]-3-iodo-2-propenyl bromide;

f) Z-3-[2-fluorophenyl]-3-iodo-2-propenyl bromide;

g) Z-3-[4-fluorophenyl]-3-iodo-2-propenyl bromide;

h) Z-3-phenyl-3-iodo-2-propenyl bromide.

Example 5

General Procedure for the synthesis of methyl Z-5-Aryl-5-iodo-2-benzophenoneimino-4-pentenoates (6)

To solution of i-Pr$_2$NH (1.2 eqv.) at −78° C. in THF was added BuLi (1.2 eqv) followed by HMPA (2.0 eqv). The reaction mixture was stirred at room temperature for 5 min. before being re-cooled to −78° C. and a solution of compound 5 (1.0 eqv) dissolved in THF added. The mixture was stirred at this temperature for 1 hr. The bromide 4 (1.2 eqv) dissolved in THF was then added and the reaction mixture allowed to warm to room temperature overnight. The mixture was poured into water and extracted with ether. The organic extract was then washed with brine and dried over anhydrous Na$_2$SO$_4$. The organic solvent was then removed in vacuo and the crude product purified by flash column chromatography.

The following compounds were prepared using the above protocol:

a) Methyl Z-5-[2,4-Difluorophenyl]-5-iodo-2-benzophenoneimino-4-pentenoate (4.1 g, 84% yield) from 5 (2.4 g, 9.3 mmol) and 4a (4.0 g, 11.1 mmol);

b) Methyl Z-5-[4-lsopropylphenyl]-5-iodo-2-benzophenoneimino-4-pentenoate (1.1 g, 44% yield) from 5 (1.2 g, 4.6 mmol) and 4b (2.0 g, 5.5 mmol);

c) Methyl Z-5-[4-$^t$butylphenyl]-5-iodo-2-benzophenoneimino-4-pentenoate from 5 (0.6 g, 1.2 mmol) and 4d;

d) Methyl Z-5-[4,4'-Biphenyl]-5-iodo-2-benzophenoneimino-4-pentenoate (0.8 g, % yield) from 5 (0.6 g, 1.2 mmol) and 4d (0.6 g, 1.5 mmol);

e) Methyl Z-5-[2-(3,5-difluorobenzyloxy)phenyl]-5-iodo-2-benzophenoneimino-4-pentenoate from 5 (0.6 g, 1.2 mmol) and 4d;

f) Methyl Z-5-[2-fluorophenyl]-5-iodo-2-benzophenoneimino-4-pentenoate from 5 (0.6 g, 1.2 mmol) and 4d;

g) Methyl Z-5-[4-fluorophenyl]-5-iodo-2-benzophenoneimino-4-pentenoate from 5 (0.6 g, 1.2 mmol) and 4d;

h) Methyl Z-5-phenyl-5-iodo-2-benzophenoneimino-4-pentenoate from 5 (0.6 g, 1.2 mmol) and 4d.

Example 6

General Procedure for the synthesis of methyl 5,5-diaryl-2-benzophenoneimino-4-pentenoates (7)

To a mixture of compound 6 or compound 13 (1 eqv), the Arylboronic acid or the boronate ester (2.0 eqv) and Pd(PPh$_3$)$_4$ (0.05 eqv) was added DME/2N Na$_2$CO$_3$ (1:1). The mixture was purged with Argon and heated to 110° C. for 20–30 min. The reaction mixture was cooled to room temperature and water added. The mixture was extracted with ethyl acetate and the organic extract washed with brine and dried over anhydrous Na$_2$SO$_4$. The organic solvent was then removed in vacuo and purified by flash column chromatography.

The following compounds were prepared using the above protocol:

a) Methyl 5-[2,4-Difluorophenyl]-5-[4-methylphenyl]-2-benzophenoneimino-4-pentenoate (0.2 g, 96% yield) from 6a (0.2 g, 0.5 mmol) and 4-methylbenzeneboronic acid (0.1 g, 0.9 mmol);

b) Methyl 5-[2,4-Difluorophenyl]-5-[3-isopropylphenyl]-2-benzophenoneimino-4-pentenoate (0.5 g, 95% yield) from 6a (0.5 g, 0.9 mmol) and 3-isopropylbenzeneboronic acid (0.3 g, 1.9 mmol);

c) Methyl 5-[2,4-Difluorophenyl]-5-[4-isopropylphenyl]-2-benzophenoneimino-4-pentenoate (0.2 g, 80% yield) from 6a (0.3 g, 0.6 mmol) and 4-isopropylbenzeneboronic acid (0.2 g, 1.1 mmol);

d) Methyl 5-[2,4-Difluorophenyl]-5-[4-t-butylphenyl]-2-benzophenoneimino-4-pentenoate (0.3 g, 94% yield) from 6a (0.3 g, 0.6 mmol) and 4-t-butylbenzeneboronic acid (0.2 g, 1.1 mmol);

e) Methyl 5-[2,4-Difluorophenyl]-5-[3,4-dimethoxyphenyl]-2-benzophenoneimino-4-pentenoate (0.2 g, 77% yield) from 6a (0.2 g, 0.5 mmol) and 3,4-dimethoxybenzeneboronic acid (0.2 g, 0.9 mmol);

f) Methyl 5-[2,4-Difluorophenyl]-5-phenyl-2-benzophenoneimino-4-pentenoate (0.2 g, 96% yield) from 6a (0.2 g, 0.5 mmol) and phenylboronic acid (0.1 g, 0.9 mmol);

g) Methyl 5-[2,4-Difluorophenyl]-5-[2,2'-biphenyl]-2-benzophenoneimino-4-pentenoate (0.2 g, 82% yield) from 6a (0.2 g, 0.5 mmol) and 2,2'-biphenylboronic acid (0.2 g, 0.9 mmol);

h) Methyl 5-[2,4-Difluorophenyl]-5-[3,3'-biphenyl]-2-benzophenoneimino-4-pentenoate (0.2 g, 91% yield) from 6a (0.2 g, 0.5 mmol) and 3,3'-biphenylboronic acid (0.2 g, 0.9 mmol);

i) Methyl 5-[2,4-Difluorophenyl]-5-[4,4'-biphenyl]-2-benzophenoneimino-4-pentenoate (0.2 g, 86% yield) from 6a (0.2 g, 0.5 mmol) and 4,4'-biphenylboronic acid (0.2 g, 0.9 mmol);

j) Methyl 5-[2,4-Difluorophenyl]-5-[2-naphthyl]-2-benzophenoneimino-4-pentenoate (0.1 g, 79% yield) from 6a (0.2 g, 0.3 mmol) and 2-naphthylboronic acid (0.1 g, 0.6 mmol);

k) Methyl 5-[2,4-Difluorophenyl]-5-[3-thienyl]-2-benzophenoneimino-4-pentenoate (0.2 g, 84% yield) from 6a (0.3 g, 0.6 mmol) and 3-thipheneboronic acid (0.1 g, 1.1 mmol);

l) Methyl 5-[2,4-Difluorophenyl]-5-[3,4-diethylphenyl]-2-benzophenoneimino-4-pentenoate (0.2 g, 83% yield) from 6a (0.2 g, 0.5 mmol) and 3,4-diethylbenzeneboronate ester (from pinacolato-diboron) (0.2 g, 1.0 mmol);

m) Methyl 5-[4-lsopropylphenyl]-5-[2,4-difluorophenyl]-2-benzophenoneimino-4-pentenoate (0.3 g, 95% yield) from 6b (0.3 g, 0.6 mmol) and 2,4-difluorobenzeneboronate ester (from pinacolato-diboron) (0. g, 1.1 mmol);

n) Methyl 5-[4-Isopropylphenyl]-5-[4-methylphenyl]-2-benzophenoneimino-4-pentenoate (0.2 g, 74% yield) from 6b (0.2 g, 0.5 mmol) and 4-methylbenzeneboronic acid (0.1 g, 0.9 mmol);

o) Methyl 5,5-bis-[4-lsopropylphenyl]-2-benzophenoneimino-4-pentenoate (0.2 g, 87% yield) from 6b (0.2 g, 0.4 mmol) and 4-isopropylbenzeneboronic acid (0.1 g, 0.8 mmol);

p) Methyl 5-[4,4-Biphenyl]-5-[2,4-difluorophenyl]-2-benzophenoneimino-4-pentenoate (quantitative yield) from 6d (0.2 g, 0.2 mmol) and 2,4-difluorobenzeneboronate ester (see above) (0.10 g, 0.4 mmol);

q) Methyl 5-[4,4-Biphenyl]-5-[4-isopropylphenyl]-2-benzophenoneimino-4-pentenoate(quantitative yield) from 6d (0.2 g, 0.2 mmol) and 4-isopropylbenzeneboronic acid (0.7 g, 0.4 mmol);

r) Methyl 5,5-bis-[2,4-difluorophenyl]-2-benzophenoneimino-4-pentenoate from 6a (0.2 g, 0.5 mmol) and 2,4-difluorobenzeneboronate ester;

s) Methyl 5-[(3,5-difluorobenzyloxy)phenyl]-5-[4-isopropylphenyl]-2-benzo-phenoneimino-4-pentenoate from 6e and 4-isopropylbenzeneboronic acid;

t) Methyl 5-[(3,5-difluorobenzyloxy)phenyl]-5-phenyl-2-benzophenoneimino-4-pentenoate from 6e and phenylboronic acid;

u) Methyl 5-[2,4-difluorophenyl]-5-[3-nitrophenyl]-2-benzophenoneimino-4-pentenoate from 6a (0.2 g, 0.5 mmol) and 3-nitrophenylboronic acid;

v) Methyl 5-[2,4-difluorophenyl]-5-[4-cyanophenyl]-2-benzophenoneimino-4-pentenoate from 6a (0.2 g, 0.5 mmol) and 4-cyanophenylboronic acid;

w) Methyl 5-[2,4-difluorophenyl]-5-[4-ethylphenyl]-2-benzophenoneimino-4-pentenoate from 6a (0.2 g, 0.5 mmol) and 4-ethylphenylboronic acid;

x) Methyl 5-[2,4-difluorophenyl]-5-[4-isopropylphenyl]-2-methyl-2-benzophenoneimino-4-pentenoate from 6a (0.2 g, 0.5 mmol) and 4-isopropylbenzeneboronic acid;

y) Methyl 5-[2,4-difluorophenyl]-5-[4-methylphenyl]-2-benzophenoneimino-4-pentenoate from 6a (0.2 g, 0.5 mmol) and 4-methylphenylboronic acid;

z) Methyl 5-[2,4-difluorophenyl]-5-[4-$^n$butylphenyl]-2-benzophenoneimino-4-pentenoate from 6a (0.2 g, 0.5 mmol) and 4-$^n$butylphenylboronic acid;

aa) Methyl 5-[2,4-difluorophenyl]-5-[4-trifluoromethylphenyl]-2-benzophenoneimino-4-pentenoate from 6a (0.2 g, 0.5 mmol) and 4-trifluoromethylphenylboronic acid;

bb) Methyl 5-[2-fluorophenyl]-5-[4-isopropylphenyl]-2-benzophenoneimino-4-pentenoate from 6f and 4-isopropylbenzeneboronic acid;

cc) Methyl 5-[4-ethylphenyl]-5-[4-fluorophenyl]-2-benzophenoneimino-4-pentenoate from 6g and 4-ethylphenylboronic acid;

dd) Methyl 5-[4-fluorophenyl]-5-[4-isopropylphenyl]-2-benzophenoneimino4-pentenoate from 6g and 4-isopropylbenzeneboronic acid;

ee) Methyl 5-[4-isopropylphenyl]-5-[4-$^t$butylphenyl]-2-benzophenoneimino-4-pentenoate from 6c and 4-isopropylbenzeneboronic acid;

ff) Methyl 5-phenyl-5-[4-$^t$butylphenyl]-2-benzophenoneimino-4-pentenoate from 6c and phenylboronic acid;

gg) Methyl 5-[2,4-difluorophenyl]-5-[4-$^t$butylphenyl]-2-benzophenoneimino-4-pentenoate from 6c and 2,4-difluorobenzeneboronate ester;

hh) Methyl 5-[4-isopropylphenyl]-5-phenyl-2-[benzophenoneimino4-pentenoate from 6h and 4-isopropylbenzeneboronic acid;

ii) Methyl 5-[4-isopropylphenyl]-5-[4-methoxyphenyl]-2-benzophenoneimino-4-pentenoate from the compound of example 10 and 4-methoxyphenylboronic acid;

jj) Methyl 5-[4-isopropylphenyl]-5-[3-thienyl]-2-benzophenoneimino-4-pentenoate the compound of example 10 and 3-thienylboronic acid;

kk) Methyl 5-[4-isopropylphenyl]-5-[3-pyridyl]-2-benzophenoneimino-4-pentenoate the compound of example 10 and 3-pyridylboronic acid.

Example 7

General Procedure for the synthesis of methyl 5,5-diaryl-2-amino-4-pentenoates (8)

A solution of compound 7 (1 eqv) in a THF/$CH_2Cl_2$/TFA/$H_2O$ mixture (1:1:0.2:0.25, by volume) was stirred at room temperature for 4 hrs. The reaction mixture was poured into saturated $NaHCO_3$ and extracted with $CH_2Cl_2$. The organic extract was washed with brine and dried over anhydrous $Na_2SO_4$. The solvent was then removed in vacuo and the product purified by flash column chromatography.

The following intermediates were prepared using the above protocol:

a) E-methyl 2-amino-5-[2,4-difluorophenyl]-5-[3-isopropylphenyl]-4-pentenoate (242 mg, 80% yield);

b) E-methyl 2-amino-5-[2,4-difluorophenyl]-5-[4-tButylphenyl]-4-pentenoate (131 mg, 85% yield);

c) E-methyl 2-amino-5-[2,4-difluorophenyl]-5-[3-thienyl]-4-pentenoate (102 mg, 87% yield);

d) E-methyl 2-amino-5-[2,4-difluorophenyl]-5-[4-isopropylphenyl]-4-pentenoate (102 mg, 83% yield);

e) E-methyl 2-amino-5-[2,4-difluorophenyl]-5-[4,4'-biphenyl]-4-pentenoate (31 mg, 20% yield);

f) E-methyl 2-amino-5-[2,4-difluorophenyl]-5-phenyl-4-pentenoate (95 mg, 70% yield);

g) E-methyl 2-amino-5-[2,4-difluorophenyl]-5-[3,4-dimethoxyphenyl]-4-pentenoate (100 mg, 76% yield);

h) E-methyl 2-amino-5-[2,4-difluorophenyl]-5-[4-methylphenyl]-4-pentenoate (108 mg, 83% yield);

i) E-methyl 2-amino-5-[2,4-difluorophenyl]-5-[3,3'-biphenyl]-4-pentenoate (72 mg, 47% yield);

j) E-methyl 2-amino-5-[2,4-difluorophenyl]-5-[2,2'-biphenyl]-4-pentenoate (123 mg, 89% yield);

k) E-methyl 2-amino-5-[2,4-difluorophenyl]-5-[2-naphthyl]-4-pentenoate (69 mg, 90% yield);

l) E-methyl 2-amino-5-[2,4-difluorophenyl]-5-[3,4-diethylphenyl]-4-pentenoate (94 mg, 56% yield);

m) Methyl 2-amino-5,5-di[4-isopropylphenyl]-4-pentenoate (120 mg, 97% yield);

n) Z-methyl 2-amino-5-[2,4-difluorophenyl]-5-[4-isopropylphenyl]-4-pentenoate (66 mg, 39% yield);

o) E-methyl 2-amino-5-[4-isopropylphenyl]-5-[4-methylphenyl]-4-pentenoate (106 mg, 85% yield);

p) Z-methyl 2-amino-5-[2,4-difluorophenyl]-5-[4,4'-biphenyl]-4-pentenoate (72 mg, 91% yield);

q) E-methyl 2-amino-5-[4-isopropylphenyl]-5-[4,4'-biphenyl]-4-pentenoate (49 mg, 61% yield);

r) Methyl 2-amino-5,5-bis-[2,4-difluorophenyl]-4-pentenoate;

s) E-methyl 2-amino-5-[(3,5-difluorobenzyloxy)phenyl]-5-[4-isopropylphenyl]-4-pentenoate;

t) E-methyl 2-amino-5-[(3,5-difluorobenzyloxy)phenyl]-5-phenyl-4-pentenoate;

u) E-methyl 2-amino-5-[2,4-difluorophenyl]-5-[3-nitrophenyl]-4-pentenoate;

v) E-methyl 2-amino-5-[2,4-difluorophenyl]-5-[4-cyanophenyl]-4-pentenoate;

w) E-methyl 2-amino-5-[2,4-difluorophenyl]-5-[4-ethylphenyl]-4-pentenoate;

x) E-methyl 2-amino-5-[2,4-difluorophenyl]-5-[4-isopropylphenyl]-2-methyl-4-pentenoate;

y) E-methyl 2-amino-5-[2,4-difluorophenyl]-5-[4-methylphenyl]-4-pentenoate;

z) E-methyl 2-amino-5-[2,4-difluorophenyl]-5-[4-*ⁿ*butylphenyl]-4-pentenoate;

aa) E-methyl 2-amino-5-[2,4-difluorophenyl]-5-[4-trifluoromethylphenyl]-4-pentenoate;

bb) E-methyl 2-amino-5-[2-fluorophenyl]-5-[4-isopropylphenyl]-4-pentenoate;

cc) E-methyl 2-amino-5-[4-ethylphenyl]-5-[4-fluorophenyl]-4-pentenoate;

dd) E-methyl 2-amin-5-[4-fluorophenyl]-5-[4-isopropylphenyl]-4-pentenoate;

ee) E-methyl 2-amino-5-[4-isopropylphenyl]-5-[4-*ᵗ*butylphenyl]-4-pentenoate;

ff) E-methyl 2-amino-5-phenyl-5-[4-*ᵗ*butylphenyl]-4-pentenoate;

gg) Z-methyl 2-amino 5-[2,4-difluorophenyl]-5-[4-*ᵗ*butylphenyl]-4-pentenoate;

hh) Z-methyl 2-amino 5-[4-isopropylphenyl]-5-phenyl-4-pentenoate;

ii) E-methyl 5-[4-isopropylphenyl]-5-[4-methoxyphenyl]-4-pentenoate;

jj) E-methyl 5-[4-isopropylphenyl]-5-[3-thienyl]-4-pentenoate;

kk) E-methyl 5-[4-isopropylphenyl]-5-[3-pyridyl]-4-pentenoate.

Example 8
General Procedure for the hydrolysis of Sodium 5,5-diaryl-2-amino4-pentenoates (9)

To a solution of compound 8 (1 eqv) in MeOH was added 1N NaOH (1 eqv.) and the mixture stirred at room temperature for 4 hrs (reaction judged complete by TLC analysis). The solvent was then removed in vacuo giving the product as a sodium salt. (Product purity was further enhanced using solid phase extraction (SPE) tube).

The following compounds were prepared using the above protocol:

a) Sodium E-2-amino-5-[2,4-difluorophenyl]-5-[3-isopropylphenyl]-4-pentenoate (yellow solid, 71 mg, quantitative yield);

b) Sodium E-2-amino-5-[2,4-difluorophenyl]-5-[4-tButylphenyl]-4-pentenoate (beige solid, 60 mg, 97% yield);

c) Sodium E-2-amino-5-[2,4-difluorophenyl]-5-[3-thienyl]-4-pentenoate (yellow solid, 57 mg, 95% yield);

d) Sodium E-2-amino-5-[2,4-difluorophenyl]-5-[4-isopropylphenyl]-4-pentenoate (pale yellow solid, 54 mg, 90% yield);

e) Sodium E-2-amino-5-[2,4-difluorophenyl]-5-[4,4'-biphenyl]-4-pentenoate (off-white solid, 17 mg, 67% yield);

f) Sodium E-2-amino-5-[2,4-difluorophenyl]-5-phenyl-4-pentenoate (off-white solid, 29 mg, 38% yield);

g) Sodium E-2-amino-5-[2,4-difluorophenyl]-5-[3,4-dimethoxyphenyl]-4-pentenoate (off-white solid, 69 mg, 94% yield);

h) Sodium E-2-amino-5-[2,4-difluorophenyl]-5-[4-methylphenyl]-4-pentenoate (white solid, 20 mg, 23% yield);

i) Sodium E-2-amino-5-[2,4-difluorophenyl]-5-[3,3'-biphenyl]-4-pentenoate (white solid, 40 mg, 75% yield);

j) Sodium E-2-amino-5-[2,4-difluorophenyl]-5-[2,2'-biphenyl]-4-pentenoate (off-white, 80 mg, 91% yield);

k) Sodium E-2-amino-5-[2,4-difluorophenyl]-5-[2-naphthyl]-4-pentenoate (white solid, 40 mg, 77% yield);

l) Sodium E-2-amino-5-[2,4-difluorophenyl]-5-[3,4-diethylphenyl]-4-pentenoate (pale yellow solid, 85 mg, 88% yield);

m) Sodium 2-amino-5,5-di[4-isopropylphenyl]-4-pentenoate (white foam, 72 mg, 71% yield);

n) Sodium Z-2-amino-5-[2,4-difluorophenyl]-5-[4-isopropylphenyl]-4-pentenoate (beige solid, 51 mg, quantitative yield);

o) Sodium E-2-amino-5-[4-isopropylphenyl]-5-[4-methylphenyl]-4-pentenoate (off-white solid, 68 mg, 88% yield);

p) Sodium Z-2-amino-5-[2,4-difluorophenyl]-5-[4,4'-biphenyl]-4-pentenoate (white solid, 15 mg, 21% yield);

q) Sodium E-2-amino-5-[4-isopropylphenyl]-5-[4,4'-biphenyl]-4-pentenoate (white solid, 30 mg, 59% yield);

r) Sodium 2-amino-5,5-bis-[2,4-difluorophenyl]-4-pentenoate (77% yield);

s) Sodium E-2-amino-5-[(3,5-difluorobenzyloxy)phenyl]-5-[4-isopropylphenyl]-4-pentenoate (17% overall yield from the coupling step);

t) Sodium E-2-amino-5-[(3,5-difluorobenzyloxy)phenyl]-5-phenyl-4-pentenoate (15% overall yield from the coupling step);

u) Sodium E-2-amino-5-[2,4-difluorophenyl]-5-[3-nitrophenyl]-4-pentenoate (quantitative yield);

v) Sodium E-2-amino-5-[2,4-difluorophenyl]-5-[4-cyanophenyl]-4-pentenoate (62% yield);

w) Sodium E-2-amino-5-[2,4-difluorophenyl]-5-[4-ethylphenyl]-4-pentenoate (quantitative yield);

x) Sodium E-2-amino-5-[2,4-difluorophenyl]-5-[4-isopropylphenyl]-2-methyl-4-pentenoate (50% yield);

y) Sodium E-2-amino-5-[2,4-difluorophenyl]-5-[4-methylphenyl]-4-pentenoate (23% yield);

z) Sodium E-2-amino-5-[2,4-difluorophenyl]-5-[4-*ⁿ*butylphenyl]-4-pentenoate (71% yield);

aa) Sodium E-2-amino-5-[2,4-difluorophenyl]-5-[4-trifluoromethylphenyl]-4-pentenoate (66% yield);

bb) Sodium E-2-amino-5-[2-fluorophenyl]-5-[4-isopropylphenyl]-4-pentenoate (72% yield);

cc) Sodium E-2-amino-5-[4-ethylphenyl]-5-[4-fluorophenyl]-4-pentenoate (71% yield);

dd) Sodium E-2-amin-5-[4-fluorophenyl]-5-[4-isopropylphenyl]-4-pentenoate (88% yield);

ee) Sodium E-2-amino-5-[4-isopropylphenyl]-5-[4-*ᵗ*butylphenyl]-4-pentenoate (61% yield);

ff) Sodium E-2-amino-5-phenyl-5-[4-*ᵗ*butylphenyl]-4-pentenoate (73% yield);

gg) Sodium Z-2-amino 5-[2,4-difluorophenyl]-5-[4-*ᵗ*butylphenyl]-4-pentenoate (85% yield);

hh) Sodium Z-2-amino 5-[4-isopropylphenyl]-5-phenyl-4-pentenoate (60% yield);

ii) Sodium E-5-[4-isopropylphenyl]-5-[4-methoxyphenyl]-4-pentenoate (87% yield);

jj) Sodium E-5-[4-isopropylphenyl]-5-[3-thienyl]-4-pentenoate (70% yield);

kk) Sodium E-5-[4-isopropylphenyl]-5-[3-pyridyl]-4-pentenoate (74% yield);

Example 9

General Procedure for the hydrostannation of Aryl Alkynes (11)

To a solution of the aryl alkyne 11 (1 eqv) and $PdCl_2(PPh_3)_2$ in THF under argon was added dropwise tributyltin hydride (1.1 eqv). The mixture was stirred at room temperature for 45 minutes. (reaction judged complete by TLC analysis). The solvent was then removed in vacuo and the crude residue was purified by flash chromatography.

Methyl 5-[4-isopropylphenyl]-5-tributylstannyl-2-benzophenoneimino-4-pentenoate 12 was prepared using the above protocol.

Example 10

General Procedure for the Tributyltin-Iodine Exchange

To a stirred solution of tributylvinyl-tin 12 (1 eqv) in $CH_2Cl_2$ at room temperature which was shielded from light was added $I_2$ (1 eqv). After 5 minutes, an aqueous solution of $Na_2S_2O_3$ (saturated) was added followed by extraction with DME. The organic layer was separated and used directly in the next step. (which was carried out according to the procedure of Example 6, above).

Methyl 5-[4-isopropylphenyl]-5-iodo-2-benzophenoneimino-4-pentenoate 13 was prepared using the above protocol.

Example 11

Assay of Transport via GlyT-2 Transporters

This example illustrates a method for the measurement of glycine uptake by transfected cultured cells.

Cells stably transfected with human GlyT-2 (the homolog of the rat GlyT-2 described by Liu et al., *J. Biological Chemistry*, 268, 1993:22802–22808) were washed twice with HEPES buffered saline (HBS). The cells were then incubated 10 minutes at 37° C., after which a solution containing 50 nM [$^3$H]glycine (17.5 Ci/mmol) and either (a) no potential competitor, (b) 10 nM glycine or (c) a concentration of a candidate drug. A range of concentrations of the candidate drug was used to generate data for calculating the concentration resulting in 50% of the effect (e.g., the $IC_{50}$'s which are the concentration of drug inhibiting glycine uptake by 50%). The cells were then incubated another 10 minutes at 37° C., after which the cells were aspirated and washed three times with ice-cold HBS. The cells were solubilized in scintillant, shaken for 30 minutes, and the radioactivity in the cells was counted using a scintillation counter. Data were compared between the same cells contacted and not contacted by the candidate agent.

All exemplified compounds of the invention were tested for inhibition of glycine transport via GlyT-2 and displayed a $pIC_{50}$ in the range of from about 4 to about 8, preferred compounds displaying a $pIC_{50}$ of greater than 6, representative (but not limiting) examples of these being Z-2-Amino-5-[4-isopropylphenyl]-5-phenyl-4-pentenoic acid, E-2-Amino-5-[2,4-difluorophenyl]-5-[4-isopropylphenyl]-4-pentenoic acid and E-2-Amino-5-[3,4-diethylphenyl]-5-[2,4-difluorophenyl]-4-pentenoic acid.

We claim:

1. A compound selected from the group consisting of a compound of formula I:

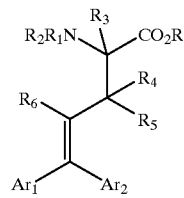

Formula I $Ar_1$ and $Ar_2$ are independently selected aryl groups, optionally substituted with substituents selected from the group consisting of alkyl, cycloalkyl, alkoxy, alkanoyl, aralkyl, aralkyloxy, halo, $NO_2$, Ph, $CF_3$, CN, OH, methylenedioxy, ethylenedioxy, $SO_2NRR'$, $NRR'$, $CO_2R$ (where R and R' are independently selected from the group consisting of H and alkyl) and a second aryl group, which may be substituted as above;

wherein any cycloalkyl or aryl substituent is linked to $Ar_1$ or $Ar_2$ by a bridging element which may be a single bond, a vinylene group, an ethynylene group, a Z group, a —Z—$(CH_2)_n$— group, a —$(CH_2)_n$—Z— group, or a —Z—$(CH_2)_n$—Z— group, where Z represents an O atom, a S atom, an NH group or an N-alkyl group, and n is an integer from 1 to 4;

wherein $Ar_1$ and $Ar_2$ may be attached to the central atom to which they are connected by a single bond, an alkylene, alkenylene or alkynylene group;

R is H, alkyl or the counter ion for a basic addition salt;

$R_1$ and $R_2$ are independently selected from the group consisting of H, alkyl and benzyl;

$R_3$, $R_4$, $R_5$ and $R_6$ are independently selected from the group consisting of H and alkyl;

and a stereoisomer, salt, solvate and hydrate thereof; with the proviso that when each of $R_1$ to $R_6$ are H, $Ar_1$ and $Ar_2$ cannot both be unsubstituted phenyl.

2. A compound according to claim 1 wherein $Ar_1$ and $Ar_2$ are each attached to the carbon atom to which they are connected by a single bond.

3. A compound according to claim 2 wherein R is H or Na.

4. A compound according to claim 3 wherein $R_3$ is H or methyl.

5. A compound according to claim 4 wherein R, $R_1$, $R_2$, $R_4$, $R_5$ and $R_6$ are H.

6. A compound according to claim 5 wherein $R_3$ is H.

7. A compound according to claim 5 wherein $Ar_1$ and $Ar_2$ are substituted phenyl.

8. A compound according to claim 7 wherein $Ar_1$ is halo-substituted phenyl.

9. A compound according to claim 8 wherein $Ar_1$ is 2,4-difluorophenyl.

10. A compound according to claim 7 wherein $Ar_2$ is alkyl-substituted phenyl.

11. A compound according to claim 10 wherein $Ar_2$ is 4-isopropyl-phenyl.

12. A compound selected from the group consisting of:
2-Amino-5,5-bis-[2,4-difluorophenyl]-4-pentenoic acid;
2-Amino-5,5-bis-[4-isopropylphenyl]-4-pentenoic acid;
E-2-Amino-5-[2-(3,5-difluorobenzyloxy)phenyl]-5-[4-isopropylphenyl]-4-pentenoic acid;

E-2-Amino-5-[2-(3,5-difluorobenzyloxy)phenyl]-5-phenyl-4-pentenoic acid;

E-2-Amino-5-[2,4-difluorophenyl]-5-[2-naphthyl]-4-pentenoic acid;

E-2-Amino-5-[2,4-difluorophenyl]-5-[3,4-dimethoxyphenyl]-4-pentenoic acid;

E-2-Amino-5-[2,4-difluorophenyl]-5-[3-isopropylphenyl]-4-pentenoic acid;

E-2-Amino-5-[2,4-difluorophenyl]-5-[3-nitrophenyl]-4-pentenoic acid;

E-2-Amino-5-[2,4-difluorophenyl]-5-[3-pyridyl]-4-pentenoic acid;

E-2-Amino-5-[2,4-difluorophenyl]-5-[3-thienyl]-4-pentenoic acid;

E-2-Amino-5-[2,4-difluorophenyl]-5-[4-cyanophenyl]-4-pentenoic acid;

E-2-Amino-5-[2,4-difluorophenyl]-5-[4-ethylphenyl]-4-pentenoic acid;

E-2-Amino-5-[2,4-difluorophenyl]-5-[4-isopropylphenyl]-2-methyl-4-pentenoic acid;

E-2-Amino-5-[2,4-difluorophenyl]-5-[4-isopropylphenyl]-4-pentenoic acid;

E-2-Amino-5-[2,4-difluorophenyl]-5-[4-methoxyphenyl]-4-pentenoic acid;

E-2-Amino-5-[2,4-difluorophenyl]-5-[4-methylphenyl]-4-pentenoic acid;

E-2-Amino-5-[2,4-difluorophenyl]-5-[4-$^n$butylphenyl]-4-pentenoic acid;

E-2-Amino-5-[2,4-difluorophenyl]-5-[4-$^t$Butylphenyl]-4-pentenoic acid;

E-2-Amino-5-[2,4-difluorophenyl]-5-[4-trifluoromethylphenyl]-4-pentenoic acid,

E-2-Amino-5-[2,4-difluorophenyl]-5-phenyl-4-pentenoic acid;

E-2-Amino-5-[2-biphenyl]-5-[2,4-difluorophenyl]-4-pentenoic acid;

E-2-Amino-5-[2-fluorophenyl]-5-[4-isopropylphenyl]-4-pentenoic acid;

E-2-Amino-5-[3,4-diethylphenyl]-5-[2,4-difluorophenyl]-4-pentenoic acid;

E-2-Amino-5-[3-biphenyl]-5-[2,4-difluorophenyl]-4-pentenoic acid;

E-2-Amino-5-[4-biphenyl]-5-[2,4-difluorophenyl]-4-pentenoic acid;

E-2-Amino-5-[4-biphenyl]-5-[4-isopropylphenyl]-4-pentenoic acid;

E-2-Amino-5-[4-ethylphenyl]-5-[4-fluorophenyl]-4-pentenoic acid;

E-2-Amino-5-[4-fluorophenyl]-5-[4-isopropylphenyl]-4-pentenoic acid;

E-2-Amino-5-[4-isopropylphenyl]-5-[4-methylphenyl]-4-pentenoic acid;

E-2-Amino-5-[4-isopropylphenyl]-5-[4-$^t$butylphenyl]-4-pentenoic acid;

E-2-Amino-5-[4-isopropylphenyl]-5-phenyl-4-pentenoic acid;

E-2-Amino-5-phenyl-5-[4-$^t$butylphenyl]-4-pentenoic acid;

Z-2-Amino-5-[2,4-difluorophenyl]-5-[4-isopropylphenyl]-4-pentenoic acid;

Z-2-Amino-5-[2,4-difluorophenyl]-5-[4-$^t$Butylphenyl]-4-pentenoic acid;

Z-2-Amino-5-[4-biphenyl]-5-[2,4-difluorophenyl]-4-pentenoic acid; and

Z-2-Amino-5-[4-isopropylphenyl]-5-phenyl-4-pentenoic acid.

13. A compound selected from the group consisting of:

E-2-Amino-5-[2,4-difluorophenyl]-5-[4-methoxyphenyl]-4-pentenoic acid;

E-2-Amino-5-[4-biphenyl]-5-[4-isopropylphenyl]-4-pentenoic acid;

E-2-Amino-5-[3-biphenyl]-5-[3,4-diethylphenyl]-4-pentenoic acid;

2-Amino-5,5-bis-[4-isopropylphenyl]-4-pentenoic acid;

Z-2-Amino-5-[4-biphenyl]-5-[2,4-difluorophenyl]-4-pentenoic acid;

E-2-Amino-5-[4-biphenyl]-5-[2,4-difluorophenyl]-4-pentenoic acid;

E-2-Amino-5-[2-biphenyl]-5-[2,4-difluorophenyl]-4-pentenoic acid;

E-2-Amino-5-[4-isopropylphenyl]-5-[4-methylphenyl]-4-pentenoic acid; and

E-2-Amino-5-[2,4-difluorophenyl]-5-phenyl-4-pentenoic acid.

14. A compound selected from the group consisting of:

E-2-Amino-5-[2-(3,5-difluorobenzyloxy)phenyl]-5-phenyl-4-pentenoic acid;

E-2-Amino-5-[3-biphenyl]-5-[2,4-difluorophenyl]-4-pentenoic acid;

E-2-Amino-5-[2,4-difluorophenyl]-5-[3-isopropylphenyl]-4-pentenoic acid;

E-2-Amino-5-[3,4-diethylphenyl]-5-[4-fluorophenyl]-4-pentenoic acid;

E-2-Amino-5-[2,4-difluorophenyl]-5-[4-$^t$Butylphenyl]-4-pentenoic acid;

E-2-Amino-5-[4-fluorophenyl]-5-[4-isopropylphenyl]-4-pentenoic acid; and

E-2-Amino-5-[2,4-difluorophenyl]-5-[4-trifluoromethylphenyl]-4-pentenoic acid.

15. A compound selected from the group consisting of:

Z-2-Amino-5-[4-isopropylphenyl]-5-phenyl-4-pentenoic acid;

E-2-Amino-5-[4-ethylphenyl]-5-[4-fluorophenyl]-4-pentenoic acid;

E-2-Amino-5-[2-fluorophenyl]-5-[4-isopropylphenyl]-4-pentenoic acid;

E-2-Amino-5-[2,4-difluorophenyl]-5-[4-isopropylphenyl]-4-pentenoic acid;

E-2-Amino-5-[2,4-difluorophenyl]-5-[4-isopropylphenyl]-2-methyl-4-pentenoic acid;

E-2-Amino-5-[2-(3,5-difluorobenzyloxy)phenyl]-5-[4-isopropylphenyl]-4-pentenoic acid, E-2-Amino-5-[3,4-diethylphenyl]-5-[2,4-difluorophenyl]-4-pentenoic acid;

E-2-Amino-5-[2,4-difluorophenyl]-5-[4-ethylphenyl]-4-pentenoic acid;

E-2-Amino-5-[2,4-difluorophenyl]-5-[4-methylphenyl]-4-pentenoic acid; and

E-2-Amino-5-[4-isopropylphenyl]-5-phenyl-4-pentenoic acid.

16. A pharmaceutical composition comprising a therapeutically effective amount of a compound of claim 1 and a pharmaceutically acceptable carrier.

17. A process for preparing a compound of Formula 9 as shown in the scheme below:

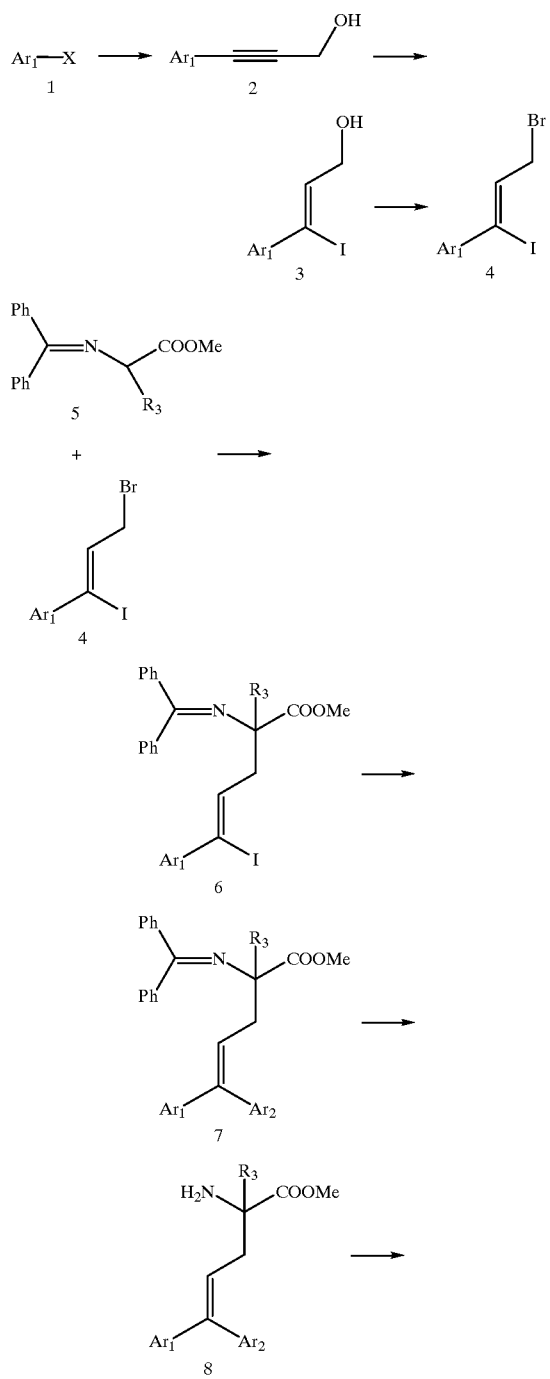

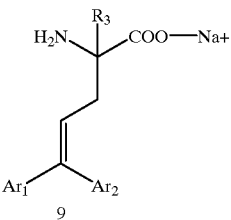

-continued

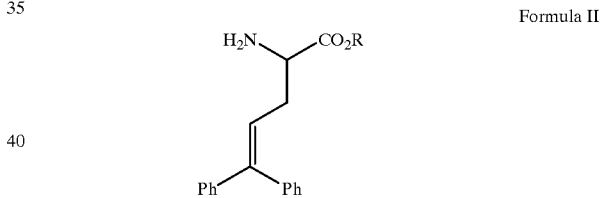

wherein,

Ar$_1$ and Ar$_2$ are independently selected aryl groups, optionally substituted with substituents selected from the group consisting of alkyl, cycloalkyl, alkoxy, alkanoyl, aralkyl, aralkyloxy, halo, NO$_2$, Ph, CF$_3$, CN, OH, methylenedioxy, ethylenedioxy, SO$_2$NRR', NNR', CO$_2$R (where R and R' are independently selected from the group consisting of H and alkyl) and a second aryl group, which may be substituted as above, wherein any cycloalkyl or aryl substituent is linked to Ar$_1$ or Ar$_2$ by a bridging element which may be a single bond, a vinylene group, an ethynylene group, a Z group, a —Z—(CH$_2$)$_n$— group, a —(CH$_2$)$_n$—Z— group, or a —Z—(CH$_2$)$_n$—Z— group, where Z represents an O atom, a S atom, an NH group or an N-alkyl group, and n is an integer from 1 to 4, and wherein Ar$_1$ and Ar$_2$ may be attached to the central atom to which they are connected by a single bond, an alkylene, alkenylene or alkynylene group;

R$_3$ is independently selected from the group consisting of H and alkyl; and

X is bromo or iodo.

18. A pharmaceutical composition comprising a therapeutically effective amount of a compound of Formula II:

Formula II $$H_2N \diagup CO_2R$$

$$Ph \diagdown Ph$$

wherein R is H, alkyl, or the counter ion for a basic addition salt, a stereoisomer, salt, solvate or hydrate thereof and a pharmaceutically acceptable carrier.

19. A method for treating a patient having a medical condition for which a glycine transport inhibitor is indicated, comprising the step of administering to the patient a pharmaceutical composition as defined in claim 16 or 18.

20. A method according to claim 19 in which the medical condition is pain or spasticity.

* * * * *